US012653568B2

(12) United States Patent
Bennett

(10) Patent No.: US 12,653,568 B2
(45) Date of Patent: Jun. 16, 2026

(54) ULTRASONIC PROBES FOR PRODUCING MULTIPLE CAVITATION VOLUMES

(71) Applicant: Solta Medical Ireland Limited, Dublin (IE)

(72) Inventor: Frederick Jay Bennett, Bellevue, WA (US)

(73) Assignee: Solta Medical Ireland Limited, Dublin (IE)

( * ) Notice: Subject to any disclaimer, the term of this patent is extended or adjusted under 35 U.S.C. 154(b) by 908 days.

(21) Appl. No.: 17/909,028

(22) PCT Filed: Mar. 15, 2021

(86) PCT No.: PCT/EP2021/056490
    § 371 (c)(1),
    (2) Date: Sep. 2, 2022

(87) PCT Pub. No.: WO2021/185738
    PCT Pub. Date: Sep. 23, 2021

(65) Prior Publication Data
    US 2023/0087566 A1     Mar. 23, 2023

Related U.S. Application Data

(60) Provisional application No. 62/991,142, filed on Mar. 18, 2020.

(51) Int. Cl.
    *A61B 17/32*     (2006.01)
    *A61B 17/00*     (2006.01)
    A61B 17/22     (2006.01)

(52) U.S. Cl.
    CPC ............... *A61B 17/320068* (2013.01); *A61B 2017/00792* (2013.01); *A61B 17/22004* (2013.01);
    (Continued)

(58) Field of Classification Search
    CPC .. A61B 17/320068; A61B 2017/00792; A61B 2017/320073; A61B 2017/320089; A61B 2017/22008; A61B 17/22004
    See application file for complete search history.

(56) References Cited

U.S. PATENT DOCUMENTS 5,205,817 A * 4/1993 Idemoto ............... A61C 8/0089
                                                    606/169
    5,879,364 A * 3/1999 Bromfield .......... A61B 17/3476
                                                    606/169
    (Continued)

FOREIGN PATENT DOCUMENTS

CN     104582605 A     4/2015
    CN     107072813 A     8/2017
    (Continued)

OTHER PUBLICATIONS

Taiwan Intellectual Property Office, Examination Report issued in Taiwanese Patent Application No. 110109143 on Jun. 4, 2024; 18 pages.
    (Continued)

*Primary Examiner* — Jing Rui Ou
(74) *Attorney, Agent, or Firm* — Thompson Hine LLP

(57) ABSTRACT
Probes for delivering ultrasonic energy and related methods. The probe includes a shank having a shaft coupling a proximal end to a distal end. The shank is configured to propagate ultrasonic energy from the proximal end to a tip of the distal end in a propagation direction parallel to a longitudinal axis disposed along a centerline of the shank. The tip may be positioned to substantially coincide with a displacement antinode position when the ultrasonic energy corresponds to odd integer multiples of a quarter wavelength of a resonance frequency. Multiple grooves within the shaft are configured to create multiple cavitation volumes in a medium proximate to the shank responsive to the ultrasonic
(Continued)

energy. The multiple grooves include a second groove intervening between a first groove and the proximal end. The first groove is positioned at a distance of an integer multiple of a half-wavelength of the resonance frequency.

11 Claims, 8 Drawing Sheets

(52) U.S. Cl.
CPC .............. *A61B 2017/22008* (2013.01); *A61B 2017/320073* (2017.08); *A61B 2017/320089* (2017.08)

(56) References Cited

U.S. PATENT DOCUMENTS

| | | | |
|---|---|---|---|
| 6,368,299 | B1 * | 4/2002 | Cimino ................... A61M 1/84 |
| | | | 604/35 |
| 9,114,245 | B2 | 8/2015 | Dietz et al. |
| 9,333,005 | B2 * | 5/2016 | Schafer .......... A61B 17/320068 |
| 11,583,306 | B2 | 2/2023 | Olson et al. |
| 11,602,770 | B2 | 3/2023 | Akagane |
| 2008/0194999 | A1 | 8/2008 | Yamaha et al. |
| 2010/0168741 | A1 | 7/2010 | Sanai et al. |
| 2011/0313345 | A1 | 12/2011 | Schafer |
| 2016/0100982 | A1 | 4/2016 | McCary |

FOREIGN PATENT DOCUMENTS

| | | | |
|---|---|---|---|
| EP | 2796170 | A1 | 10/2014 |
| JP | S63-302842 | A | 12/1988 |
| JP | 2008521547 | A | 6/2008 |
| JP | 2013501599 | A | 1/2013 |
| JP | 2013530739 | A | 8/2013 |
| WO | 9944514 | A1 | 9/1999 |
| WO | 2010076873 | A1 | 7/2010 |
| WO | 2017119099 | A1 | 7/2017 |

OTHER PUBLICATIONS

Japanese Patent Office, Notice of Allowance issued in Japanese Patent Application No. 2022-555775 on Aug. 4, 2025; 2 pages.

China National Intellectual Property Administration, Notification of Allowance issued in Chinese Patent Application No. 202180021913X on Mar. 18, 2025; 4 pages.

European Patent Office, Communication under Rule 71(3) EPC, Intention to Grant, issued in European Patent Application No. 21712978.2 on Jul. 17, 2025; 6 pages.

IP Australia, Australian Patent Office, Examination Report No. 1 issued in Australian Patent Application No. 2021237684 on Nov. 6, 2025; 4 pages.

Taiwan Intellectual Property Office, Rejection Decision issued in Taiwanese Patent Application No. 110109143 on Jan. 8, 2025; 6 pages.

Ministry of Intellectual Property of South Korea, Notice of Preliminary Rejection issued in Korean Patent Application No. 10-2022-7035589 on Sep. 26, 2025; 24 pages.

European Patent Office, Communication pursuant to Article 94(3) EPC issued in European Patent Application No. 21712978.2 on Jun. 5, 2024; 5 pages.

European Patent Office, International Search Report and Written Opinion issued in International Patent Application No. PCT/EP2021/056490, 15 pages (Jun. 17, 2021).

Japan Patent Office, Notice of Reasons for Rejection issued in Japanese Patent Application No. 2022-555775 on Apr. 2, 2025; 6 pages.

Japan Patent Office, Notice of Reasons for Rejection issued in Japanese Patent Application No. 2022-555775 on Nov. 13, 2024; 12 pages.

Taiwan Intellectual Property Office, Allowance Decision issued in Taiwanese Patent Application No. 110109143 on May 20, 2025; 3 pages.

China National Intellectual Property Administration, First Office Action and Search Report issued in Chinese Patent Application No. 202180021913.X on Sep. 30, 2024; 18 pages.

IP Australia, Australian Patent Office, Notice of Acceptance for Patent Application issued in Australian Patent Application No. 2021237684 on Jan. 7, 2026; 3 pages.

* cited by examiner

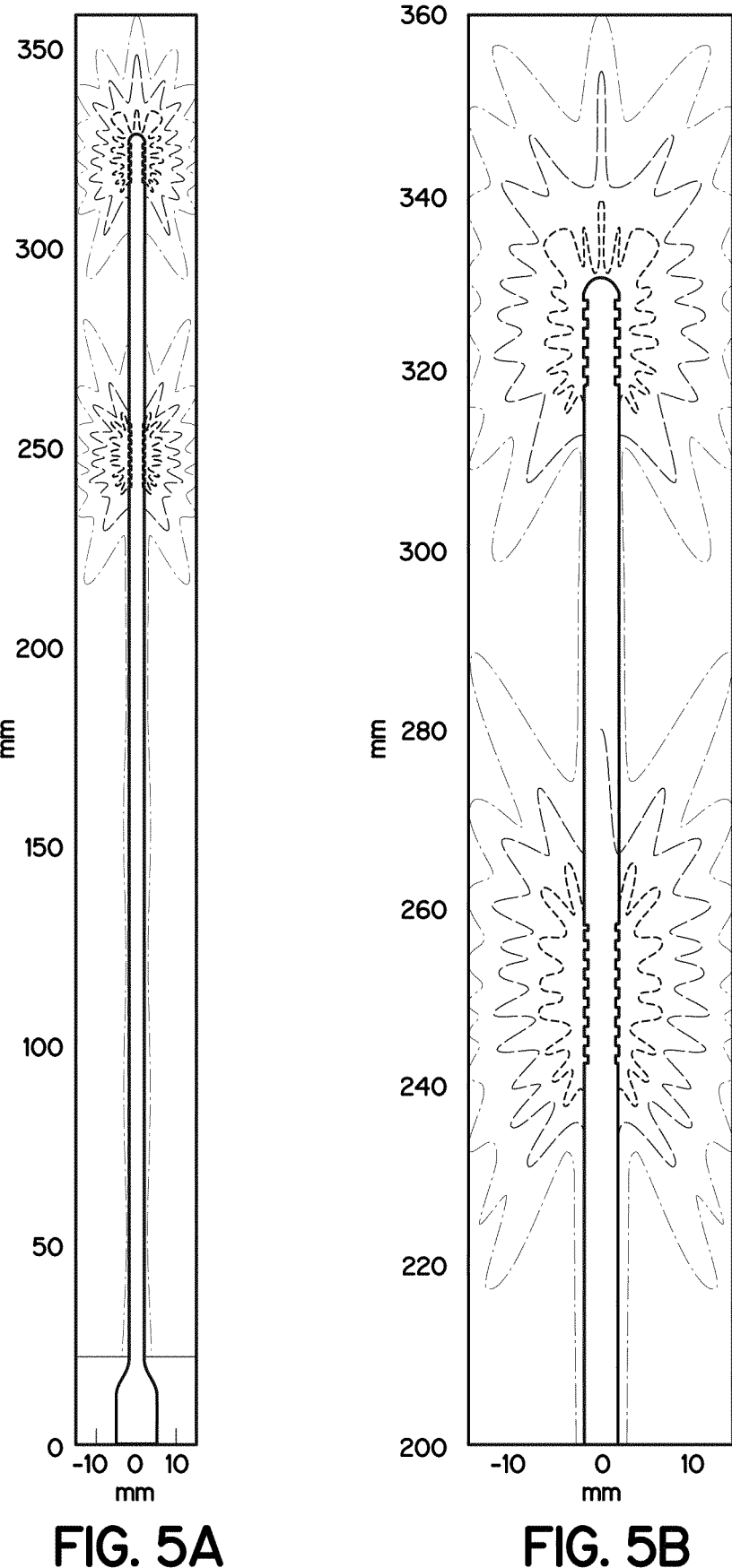
FIG. 5A                    FIG. 5B

ULTRASONIC PROBES FOR PRODUCING MULTIPLE CAVITATION VOLUMES

TECHNICAL FIELD

The invention described herein relates generally to devices for delivering ultrasonic energy as part of a cosmetic procedure, and in particular, to probes for delivering ultrasonic energy during a cosmetic procedure and related methods.

BACKGROUND

Devices deliver ultrasonic energy towards a targeted area of a patient for various cosmetic procedures, such as ultrasonic fragmentation or emulsification of soft tissues of the patient. When such devices are used for ultrasonic fragmentation or emulsification of soft tissues, a cavitation volume is created by interactions between the ultrasonic energy and portions of the soft tissue proximate to a tip of an ultrasonic probe delivering the ultrasonic energy. A cosmetic procedure implemented using such ultrasonic probes may involve repositioning the tip of a given ultrasonic probe to bring the tip within proximity of each area of soft tissue being targeted by the cosmetic procedure. Each instance of repositioning extends a duration of the cosmetic procedure, which contributes to operator fatigue and patient discomfort.

Thus, it may be desirable to provide ultrasonic probes capable of reducing the duration of such cosmetic procedures to avoid such adverse consequences.

SUMMARY

Embodiments of the invention described herein include ultrasonic probes ("probes") for use in a device configured to deliver ultrasonic energy as part of a cosmetic procedure and methods of performing cosmetic procedures using such ultrasonic probes. In an embodiment, a probe includes a shank having a proximal end, a distal end, and a shaft coupling the proximal end to the distal end. The proximal end is configured to couple to an ultrasonic source configured to generate ultrasonic energy. The shank is configured to propagate the ultrasonic energy from the proximal end to a tip of the distal end in a propagation direction parallel to a longitudinal axis disposed along a centerline of the shank. The tip may be positioned to substantially coincide with a displacement antinode position when the ultrasonic energy corresponds to an odd integer multiple of a quarter wavelength of a resonance frequency of the shank. A plurality of grooves within the shaft are configured to create cavitation volumes in a medium proximate to the shank responsive to the ultrasonic energy. The plurality of grooves includes a first groove located proximate to the tip and a second groove intervening between the first groove and the proximal end. The first groove is positioned at a distance of an integer multiple of a half-wavelength of the resonance frequency in the propagation direction from the second groove.

In an embodiment, a method includes accessing a probe including a shank having a proximal end, a distal end, and a shaft coupling the proximal end to the distal end. The proximal end is configured to couple to an ultrasonic source configured to generate ultrasonic energy. The shank is configured to propagate the ultrasonic energy from the proximal end to a tip of the distal end in a propagation direction parallel to a longitudinal axis disposed along a centerline of the shank. The tip is positioned to substantially coincide with a displacement antinode position when the ultrasonic energy corresponds to an odd integer multiple of a quarter wavelength of a resonance frequency of the shank. The shaft comprises a plurality of grooves configured to create cavitation volumes in a medium proximate to the shank responsive to the ultrasonic energy. The plurality of grooves includes a first groove located proximate to the tip and a second groove intervening between the first groove and the proximal end. The first groove is positioned at a distance of an integer multiple of a half-wavelength of the resonance frequency in the propagation direction from the second groove. The method further comprises inserting a portion of the probe comprising at least a subset of the plurality of grooves into biological tissue of a patient. The method further comprises causing the ultrasonic source to generate the ultrasonic energy.

In an embodiment, an ultrasonic probe includes a shank having a proximal end, a distal end, and a shaft coupling the proximal end to the distal end. The proximal end of the shank is configured to be coupled to a source of ultrasonic energy. The shaft includes a first plurality of grooves, a second plurality of grooves, and a non-grooved section positioned along a longitudinal axis of the shaft between the first plurality of grooves and the second plurality of grooves.

In an embodiment, an ultrasonic probe includes a shank having a proximal end, a distal end, and a shaft coupling the proximal end to the distal end. The proximal end is configured to be coupled to a source of ultrasonic energy. The shaft includes a plurality of grooves arranged along an entire length of the shaft.

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

BRIEF DESCRIPTION OF THE DRAWINGS

The accompanying drawings, which are incorporated in and constitute a part of this specification, illustrate various embodiments of the invention and, together with the general description of the invention given above, and the detailed description of the embodiments given below, serve to explain the embodiments of the invention. In the drawings, like reference numerals are used to indicate like parts in the various views.

FIGS. 5A-5B illustrate example loss fields obtained by simulating an ultrasonic probe delivering ultrasonic energy to a patient via the example shank depicted in FIG. 2.

3

Figures 1, 2:
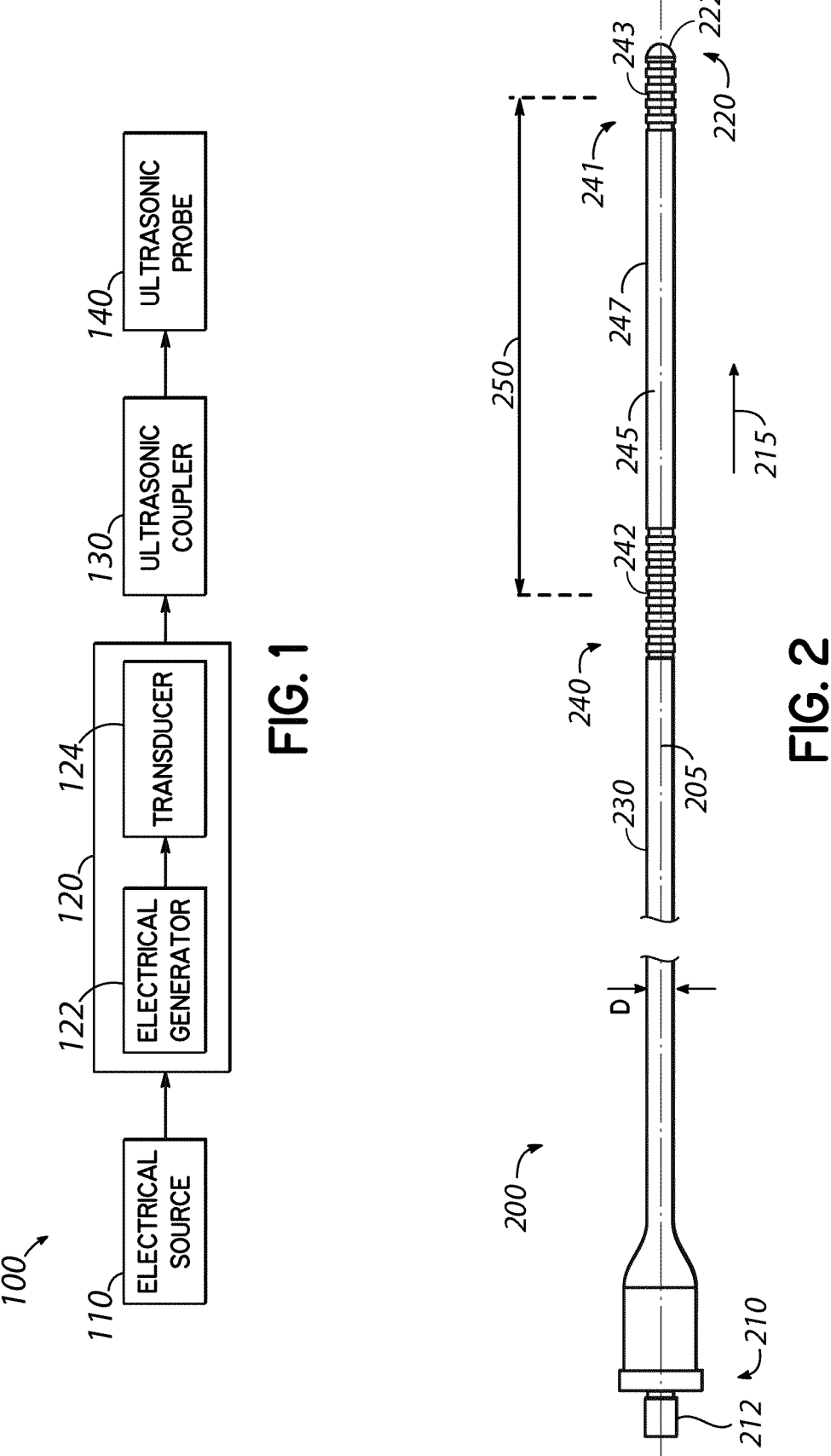
FIG. 1 is a block diagram of an example device that is suitable for implementing aspects of the invention described herein.
FIG. 2 is a side view of an example shank for an ultrasonic probe that is suitable for implementing aspects of the invention described herein.
Figures 6A, 6B:
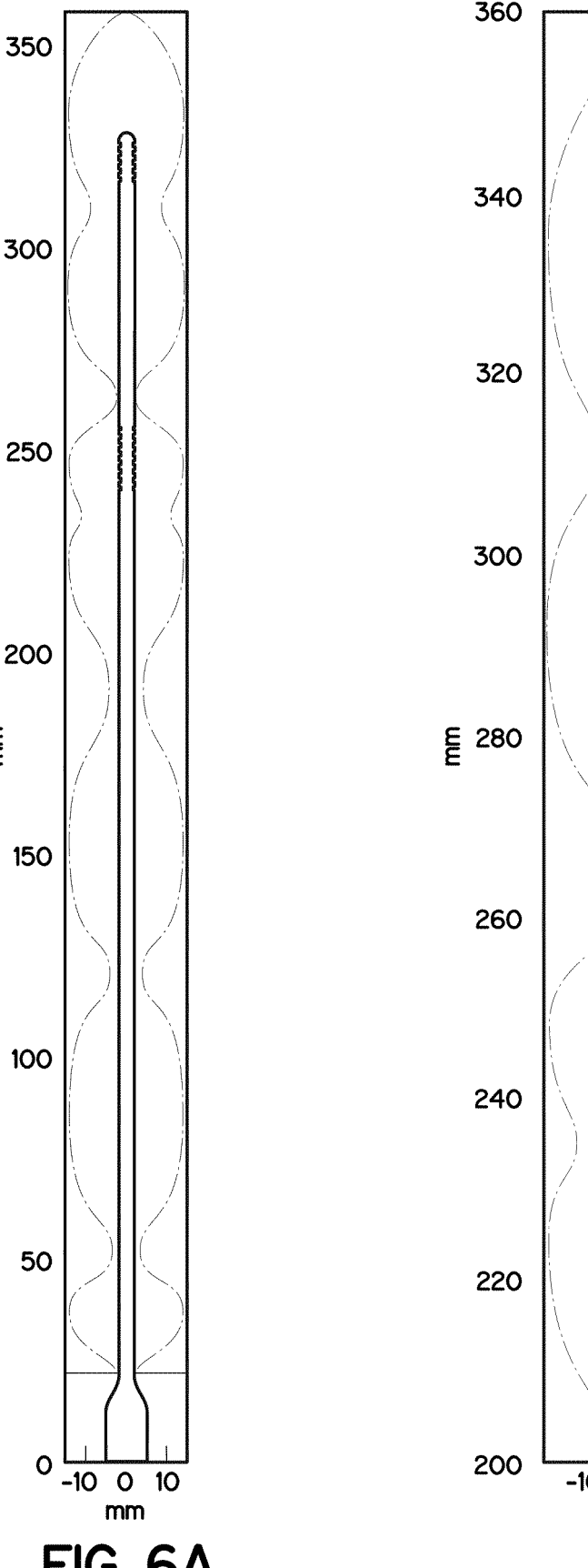

FIGS. 6A-6B illustrate example cavitation fields obtained by simulating an ultrasonic probe delivering ultrasonic energy to a patient via the example shank depicted in FIG. 2.

Figures 7A, 7B:
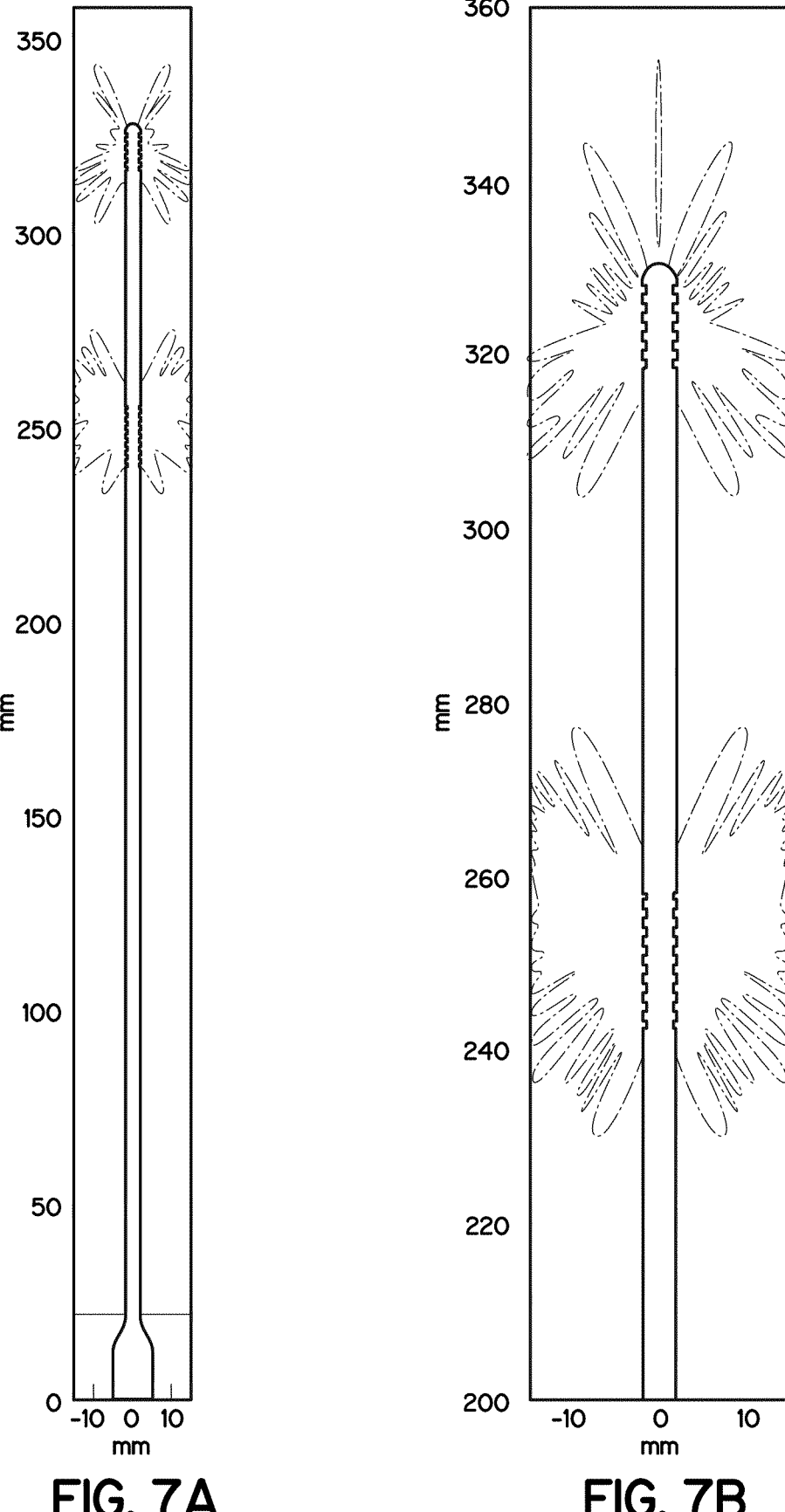

FIGS. 7A-7B illustrate example pressure fields obtained by simulating an ultrasonic probe delivering ultrasonic energy to a patient via the example shank depicted in FIG. 2.

Figures 8, 9, 10:
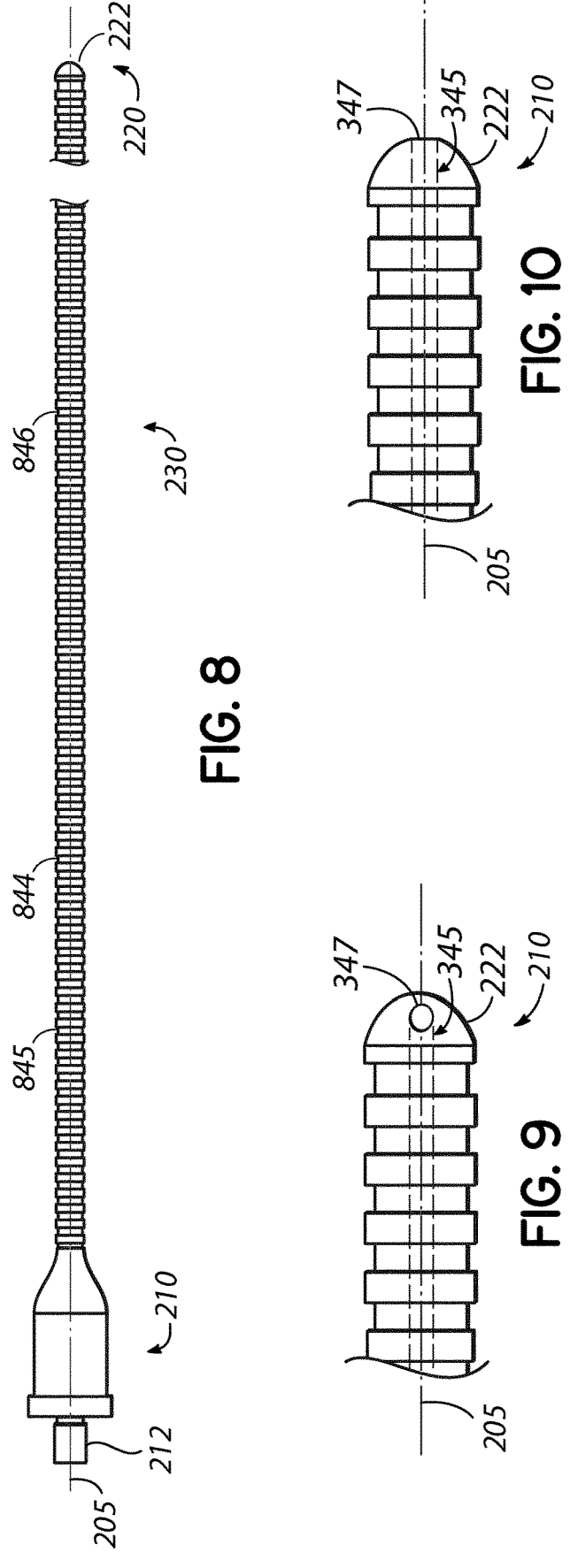

FIG. 8 is a side view of a probe having multiple grooves extending along an entire length of the shank that is suitable for implementing aspects of the invention described herein.

FIGS. 9 and 10 are side views of probe tips that may be suitable for implementing aspects of the invention described herein.

DETAILED DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein.

Referring now to FIG. 1 is a block diagram of an example device 100 that is suitable for implementing aspects of the invention described herein. In operation, device 100 is configured to deliver ultrasonic energy towards a targeted area of a patient, as part of a cosmetic procedure (e.g., ultrasonic fragmentation or emulsification of soft tissues of the patient). As depicted in FIG. 1, device 100 includes power supply 110, ultrasonic source 120, ultrasonic coupler 130, and ultrasonic probe 140. Power supply (i.e., an electrical source) 110 is configured to deliver electrical power from an external power source (e.g., an alternating current ("AC") outlet) to the various components of device 100, such as ultrasonic source 120. In an embodiment, power supply 110 is configured to convert alternating AC power obtained from an external power source into direct current ("DC") power for delivery to the various components. In an embodiment, power supply 110 is configured to provide electrical isolation between the external power source and the other components of device 100.

Ultrasonic source 120 is generally configured to generate ultrasonic energy for driving ultrasonic probe 140. To that end, ultrasonic source 120 includes electrical generator 122 and transducer 124. Electrical generator 122 is configured to generate electrical energy of a specific frequency (e.g., 36 kHz) responsive to activation by an operator of device 100. Transducer 124 is configured convert electrical energy generated by electrical generator 122 into mechanical motion or ultrasonic vibrational energy ("ultrasonic energy"). To that end, transducer is configured to expand and contract to create longitudinal compression waves in ultrasonic probe 140 via ultrasonic coupler 130. In an embodiment, transducer 124 comprises an ultrasonic motor, a piezoelectric transducer, or a combination thereof. Ultrasonic coupler 130 is configured to mechanically couple ultrasonic source 120 to ultrasonic probe 140 thereby conveying ultrasonic energy from ultrasonic coupler 130 to a shank (e.g., shank 200 of FIG. 2) detachably coupled with ultrasonic probe 140. In an embodiment, ultrasonic coupler 130 comprises a mechanical wave amplifier.

In an embodiment, ultrasonic source 120 is configured to operate in a continuous mode of operation. In this embodiment, the continuous mode of operation involves ultrasonic source 120 continuously generating ultrasonic energy. In an embodiment, ultrasonic source 120 is configured to operate in a pulsed mode of operation. In this embodiment, the pulsed mode of operation involves ultrasonic source 120 cycling between a first state and a second state while generating ultrasonic energy. During the first state, ultrasonic source 120 generates ultrasonic energy for driving ultrasonic probe 140. During the second state, ultrasonic source 120 ceases to generate ultrasonic energy for driving ultrasonic probe 140.

FIG. 2 is a side view of an example shank 200 for the ultrasonic probe 140 of FIG. 1 that is suitable for implementing aspects of the invention described herein. As depicted in FIG. 2, shank 200 includes a proximal end 210, a distal end 220, and a shaft 230 coupling the proximal end 210 to the distal end 220. Proximal end 210 includes a coupling element 212 (e.g., a stud) configured to couple shank 200 with an ultrasonic source (e.g., ultrasonic source 120 of FIG. 1). Shank 200 further includes multiple grooves (e.g., groove 242 and groove 243) along shaft 230 that are configured to generate or create cavitation volumes in a medium (e.g., biological tissue of a patient) proximate to shank 200 during a cosmetic procedure, as described in greater detail below. Shank 200 has a longitudinal axis 205 that may be disposed along a centerline of the shank 200.

As used herein, a "groove" is a discrete region of shaft 230 having a decreased cross-sectional area (with respect to a plane orthogonal to longitudinal axis 205) extending in a radially inward direction with respect to longitudinal axis 205. In an embodiment, the decreased cross-sectional area of the discrete region of shaft 230 corresponding to the groove has a diameter that is smaller than an outer diameter of shaft 230. In an embodiment, the grooves may be formed in shaft 230 by machining a substantially smooth shank 200. In an embodiment, the shaft 230 may be composed of titanium or a titanium alloy.

In FIG. 2, the multiple grooves 242, 243 are arranged along the length of the shaft 230 in multiple discrete groupings that include grouping 240 containing grooves 242 and grouping 241 containing grooves 243. The shaft 230 of the shank 200 has a non-grooved section 245 positioned between the grouping 240 of grooves 242 and the grouping 241 of grooves 243. The shaft 230 of the shank 200 has an outer surface 247 and, for round embodiments, the shaft 230 of the shank 200 may have a uniform or constant diameter, D, along its entire length with the exception of the location of the grouping 240 of grooves 242 and the grouping 241 of grooves 243. In particular, the non-grooved section 245 may have the diameter, D, and the outer surface 247 may extend unbroken (i.e., without grooving) in the non-grooved section 245 between the grouping 240 of grooves 242 and the grouping 241 of grooves 243. In an embodiment, the grooves 242, 243 may extend about the entire circumference of the shaft 230. In an embodiment, the grooves 242, 243 may be recessed relative to the outer surface 247 and about the entire circumference of the shaft 230.

Various implementations and arrangements exist for the multiple grooves of shaft 230 in accordance with embodiments of the invention described herein. For example, FIGS. 3A-3E illustrate detailed side views of a portion of shaft 230 depicting embodiments of grooves 242 with different cross-sectional profiles (with respect to a plane extending transverse to longitudinal axis 205).

Figures 3A, 3B, 3C, 3D, 3E:
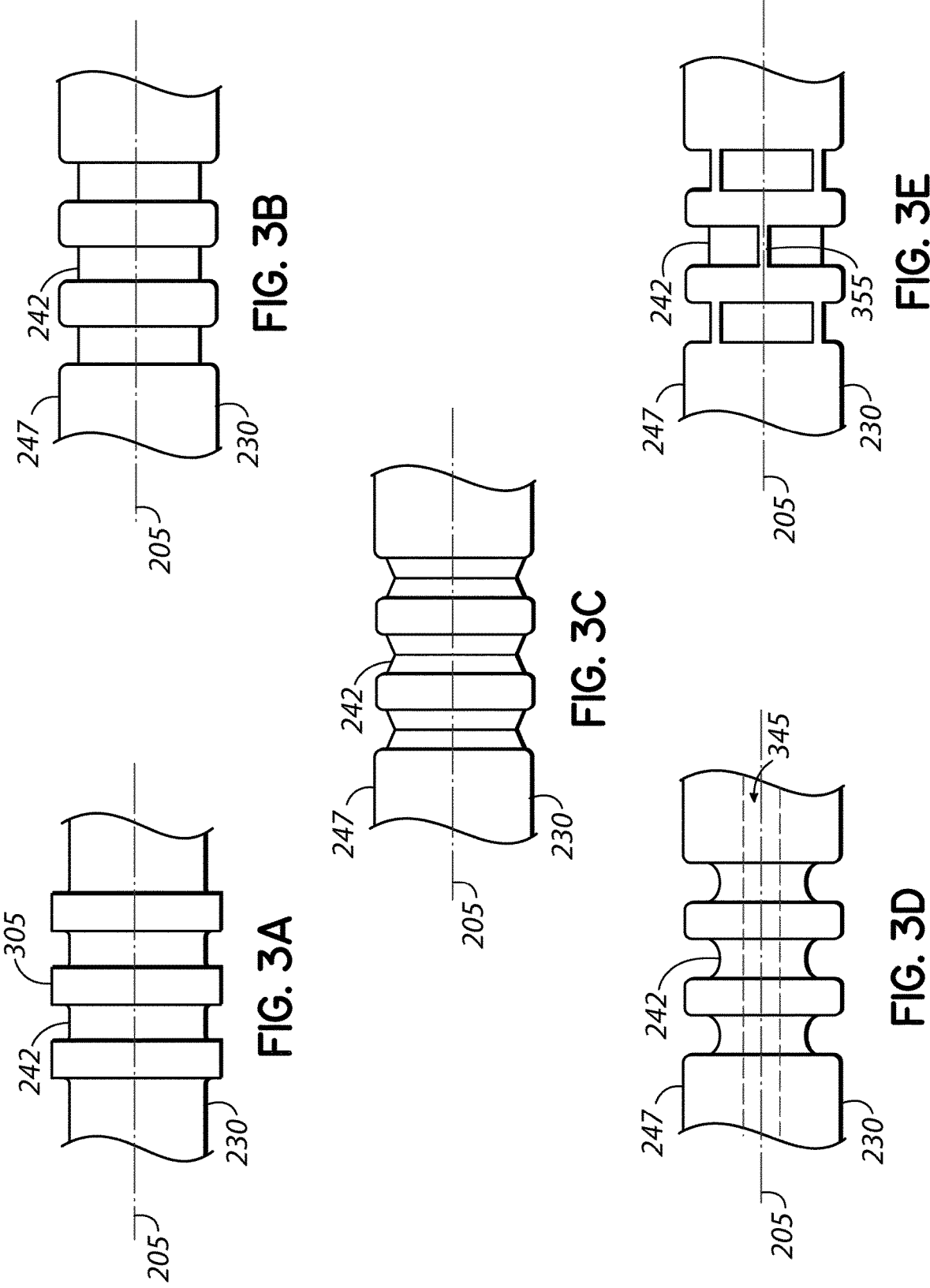
FIGS. 3A-3E are detailed side views of different types of grooves that may be suitable for implementing aspects of the invention described herein.

In FIG. 3A, the portion of shaft 230 may include flanges 305 that define the different grooves 242. As illustrated by FIG. 3A, each flange 305 represents a discrete region of shaft 230 having an increased cross-sectional area extending in a radially outward direction with respect to a longitudinal axis 205. In an embodiment, a discrete region of shaft 230 defined by flanges 305 may have a diameter equal or substantially equal to an outer diameter of shaft 230. Each groove 242 is positioned between an adjacent pair of the flanges 305.

In FIG. 3B, each groove 242 may be implemented in the portion of shaft 230 with a "Box-shaped" cross-sectional profile. As illustrated by FIG. 3B, the "Box-shaped" cross-sectional profile of each groove 242 is defined by a pair of opposing side walls and a lower surface coupling the pair of opposing side walls. Each opposing side wall of the pair of opposing side walls illustrated in FIG. 3B is configured to be substantially orthogonal to longitudinal axis 205 and the lower surface is configured to be substantially parallel to longitudinal axis 205.

In FIG. 3C, each groove 242 may be implemented in the portion of shaft 230 with a "V-shaped" cross-sectional profile. In FIG. 3D, each groove 242 is implemented in the portion of shaft 230 with a "U-shaped" cross-sectional profile. In FIG. 3E, each groove 242 in the portion of shaft 230 is interrupted by one or more ridges 355. As such, while each groove 242 in FIGS. 3B-3D is illustrated as substantially circumscribing shaft 230, FIG. 3E illustrates each groove 242 as not substantially circumscribing shaft 230 and instead only extending about a part of shaft 230.

Returning to FIG. 2, an ultrasonic source (e.g., ultrasonic source 120 of FIG. 1) is coupled to shank 200 via a coupling element 212 (e.g., a stud) positioned at the proximal end 210. Shank 200 is generally configured to propagate ultrasonic energy generated by the ultrasonic source between proximal end 210 and a tip 222 at a distal end 220. The ultrasonic energy is launched in a propagation direction 215 that is parallel to the longitudinal axis 205 disposed along a centerline of shank 200. In particular, the ultrasonic energy generated by the ultrasonic source excites a longitudinal mode of shank 200 causing shank 200 to vibrate axially creating longitudinal compression waves within shank 200. The longitudinal compression waves propagate along shank 200 from the proximal end 210 toward the distal end 220 in the propagation direction 215 and are reflected at tip 222 in a direction opposing the propagation direction 215 thereby producing a standing wave pattern.

That standing wave pattern causes certain positions (nodes) of shank 200 to experience minimal or zero vibratory movement (i.e., minimum vibration amplitude) and other positions (antinodes) of shank 200 to experience maximum vibratory movement (i.e., maximum vibration amplitude). As ultrasonic energy propagates along shank 200, portions of shaft 230 proximate to such node positions experience minimal or zero displacement amplitude while portions of shaft 230 proximate to such antinode positions experience a maximum displacement amplitude. In an embodiment, such node and antinode positions are referenced herein as "displacement node positions" and "displacement antinode positions", respectively.

In an embodiment, one of the grooves 242 in the grouping 240 may be spaced along the length of the shaft 230 from one of the grooves 243 in the grouping 241 by a distance equal to a full wavelength of a resonance frequency of shank 200. In an embodiment, one of the grooves 242 in the grouping 240 may be spaced along the length of the shaft 230 from one of the grooves 243 in the grouping 241 by a distance equal to a half-wavelength of a resonance frequency of shank 200. In an embodiment, the grooves 242 in the grouping 240 may be located approximately equidistant from the proximal end 210 and the distal end 220 of the shank 200. For a resonance frequency of 33 kHz, the distance between the groupings 240, 241 may be equal to about 60 cm to about 90 cm. In some embodiments, the distance between the groupings 240, 241 is at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 cm. In some embodiments, the distance between the groupings 240, 241 is at most about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 cm. In some embodiments, the distance between the groupings 240, 241 is about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 cm.

FIGS. 4A-4H are illustrating examples of various longitudinal compression waves created within shank 200 of an ultrasonic probe responsive to being driven by different odd integer multiples of a quarter wavelength of a resonance frequency of shank 200. Each plot or graph depicted by FIGS. 4A-4H illustrates a respective example longitudinal compression wave by plotting normalized displacement amplitude as a function of position along a normalized length of shank 200. In each graph depicted by FIGS. 4A-4H, the normalized length of shank 200 ranges from "0.0" representing a position at which proximal end 210 couples with the ultrasonic source to "1.0" representing a position of tip 222. Normalized displacement amplitude values in FIGS. 4A-4H corresponding to dashed curves represent raw values whereas normalized displacement amplitudes corresponding to solid curves represent absolute values of the raw values. Each point of inflection within the graphs depicted by FIGS. 4A-4H represents a displacement node position and each point of concavity within those graphs represents a displacement antinode position.

The graphs of the longitudinal compression waves created within shank 200 are determined using the following equations:

$$w_n = \frac{(2n-1)\pi c}{2L}$$

$$u(x) = \sin\left(\frac{w_n x}{c}\right)$$

in which $f_n$ is the resonant frequency, $w_n$ is the angular frequency determined from the resonant frequency, c is the acoustic velocity of the probe, L is the length of the probe, n is a positive integer, and x is the position along the length of the probe.

One aspect of the invention illustrated by FIGS. 4A-4H is that tip 222 is positioned along the length of the shank 200 to substantially coincide with a displacement antinode position when shank 200 is driven by ultrasonic energy comprising an odd integer multiple of a quarter wavelength of the resonance frequency of shank 200. Another aspect of the invention illustrated by FIGS. 4A-4H is that positioning tip 222 to substantially coincide with a displacement antinode position in such instances may involve configuring proximal end 210 to couple to the ultrasonic source at a point that substantially coincides with a displacement node position.

Figures 4A, 4B, 4C, 4D:
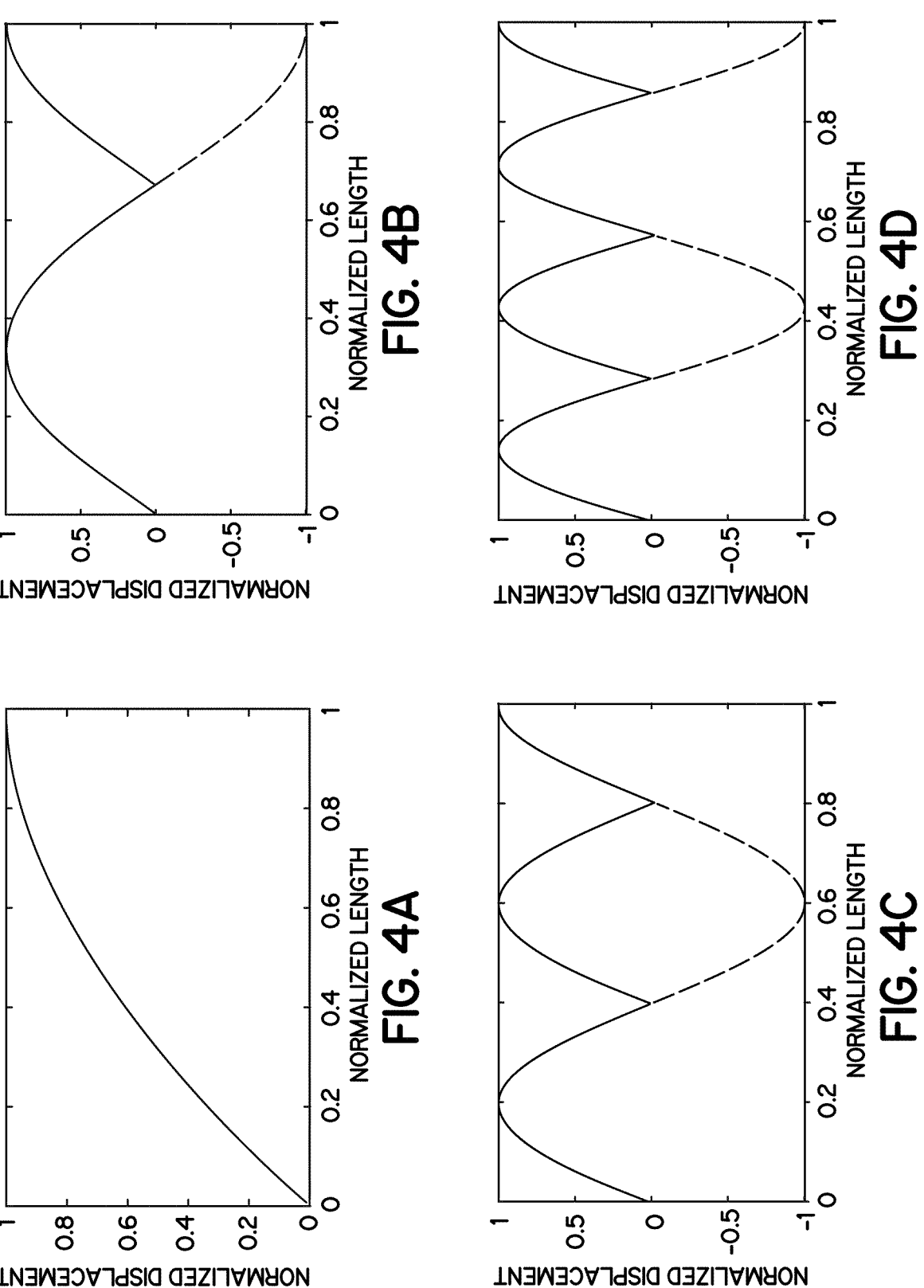
FIGS. 4A-4H are graphs illustrating examples of various longitudinal compression waves created within a shank of an ultrasonic probe responsive to being driven by different odd integer multiples of a quarter wavelength of a resonance frequency of the shank.

Another aspect of the invention illustrated by FIGS. 4A-4H is that a number of displacement antinode positions within shank 200 increase as a frequency of ultrasonic energy driving shank 200 increases. For example, in FIG. 4A, one displacement antinode position exists at the "1.0" normalized length position corresponding to tip 222 when the ultrasonic energy driving shank 200 corresponds to one quarter wavelength of a resonance frequency of shank 200. In FIG. 4B, when the ultrasonic energy driving shank 200 corresponds to three quarter wavelengths of the resonance frequency, two displacement antinode positions exist: one displacement antinode position at the "1.0" normalized length position corresponding to tip 222; and another displacement antinode position at approximately a "0.35" normalized length position. In an embodiment, a groove may be placed at each of the displacement antinode positions.

Figures 4E, 4F, 4G, 4H:

FIGS. 4C-4H illustrate that the number of displacement antinode positions continues to increase as the frequency of ultrasonic energy driving shank 200 continues to increase. In FIG. 4C, three displacement antinode position exist when the ultrasonic energy driving shank 200 corresponds to five quarter wavelengths (i.e., 1.25 wavelength resonance) of the resonance frequency. In FIG. 4D, four displacement antinode positions exist when the ultrasonic energy driving shank 200 corresponds to seven quarter wavelengths (i.e., 1.75 wavelength resonance) of the resonance frequency. In FIG. 4E, five displacement antinode positions exist when the ultrasonic energy driving shank 200 corresponds to nine quarter wavelengths (i.e., 2.25 wavelength resonance) of the resonance frequency. In FIG. 4F, six displacement antinode positions exist when the ultrasonic energy driving shank 200 corresponds to eleven quarter wavelengths (i.e., 2.75 wavelength resonance) of the resonance frequency. In FIG. 4G, seven displacement antinode positions exist when the ultrasonic energy driving shank 200 corresponds to thirteen quarter wavelengths (i.e., 3.25 wavelength resonance) of the resonance frequency. In FIG. 4H, eight displacement antinode positions exist when the ultrasonic energy driving shank 200 corresponds to fifteen quarter wavelengths (i.e., 3.75 wavelength resonance) of the resonance frequency.

Another aspect of the invention illustrated by FIGS. 4A-4H is that when multiple displacement antinode positions and/or displacement antinode positions exist along shank 200, such displacement node/antinode positions cyclically repeat in half-wavelength intervals. For example, three displacement antinode positions exist along shaft 230 in FIG. 4C. In this example, one wavelength cycle of the example longitudinal compression wave appears between the "0.00" normalized length position and approximately a "0.80" normalized length position. Within that one wavelength cycle, a first displacement antinode position exists at approximately a "0.20" normalized wavelength position and a second displacement antinode position exists approximately a "0.60" normalized wavelength position. FIG. 4C depicts the first and second displacement antinode positions occurring within that one wavelength cycle as being separated by a distance corresponding to one half-wavelength of the resonance frequency driving shank 200. FIGS. 4B and 4D-4H similarly depict displacement node positions and/or displacement antinode positions alternating along shaft 230 at intervals of one-half-wavelength.

As discussed above, the ultrasonic energy propagated by shank 200 during a cosmetic procedure induces longitudinal vibratory movement in shank 200. That ultrasonic energy generates localized heat in a medium (e.g., biological tissue of a patient) proximate to shank 200 through frictional contact between regions of shank 200 corresponding to displacement antinode positions and the medium. In various embodiments of the invention described herein, multiple grooves may be positioned along a shaft of a shank (e.g., shank 200) to substantially coincide with displacement antinode positions. Such grooves, which are not located proximate to a tip of the shaft provide the shank with additional regions at which propagating ultrasonic energy interacts with a proximate medium to generate localized heat during a cosmetic procedure. In as much as a number of displacement antinode positions and locations of such positions may be varied by varying a frequency of the ultrasonic energy driving the shank, spatial locations of cavitation volumes generated or created by the grooves in the proximate medium may also be varied, as discussed below with respect to FIG. 8.

FIGS. 5A-5B illustrate example loss fields obtained by an ultrasonic probe delivering ultrasonic energy to a patient during a simulated cosmetic procedure via shank 200 of FIG. 2. In particular, FIG. 5A illustrates the example loss fields along a length of shank 200 and FIG. 5B provides a close-up view of the example loss fields of FIG. 5A proximate to a region of shank 200 that includes the grooves. In FIGS. 5A-5B, regions at which the greatest interactions between the propagating ultrasonic energy and nearby medium (i.e., areas of high intensity) occur are diagrammatically depicted in dot-dashed lines with other regions being characterized by lower interactions between the propagating ultrasonic energy and nearby medium. High intensity areas indicate high relative spatial heating, which is proportional to cavitation. The loss fields were determined by finite elements analysis techniques.

FIGS. 5A-5B illustrate two regions of maximum loss, namely a region centered at approximately 320 millimeters ("mm"); and a second region centered at approximately 250 mm. In an embodiment and with reference to FIG. 2, the region centered at approximately 320 mm corresponds to a portion of the medium proximate to discrete groove grouping 241 and the region centered at approximately 250 mm corresponds to a portion of the medium proximate to the discrete groove grouping 240. In this embodiment, a groove 243 included in the discrete groove grouping 241 is centered at approximately 320 mm and a groove 242 included in the discrete groove grouping 240 is centered at approximately 250 mm. In this embodiment, a central groove 242 of the discrete groove grouping 240 and a central groove 243 of the discrete groove grouping 241 may be separated by a distance 250 that substantially coincides with an integer multiple of a half-wavelength of a resonance frequency of shaft 230. In this embodiment, the distance 250 may be measured between a non-central groove 242 of the discrete groove grouping 240 and a non-central groove 243 of the discrete groove grouping 241.

FIGS. 6A-6B illustrate ultrasonic energy-related pressure fields obtained by simulating an ultrasonic probe delivering ultrasonic energy to a patient via shank 200 of FIG. 2. In particular, FIG. 6A illustrates the simulated pressure fields along a length of shank 200 and FIG. 6B provides a close-up view of the simulated pressure fields of FIG. 6A proximate to a portion of shank 200 that includes the grooves 242 and the grooves 243. The pressure fields were determined by finite elements analysis techniques. The maximum pressure field occurs in the shaft along its entire length, and local maxima in the pressure fields occur in the medium as indicted by the dot-dashed lines.

FIGS. 7A-7B illustrate simulated cavitation fields obtained by simulating an ultrasonic probe delivering ultrasonic energy to a patient via shank 200 of FIG. 2. In particular, FIG. 7A illustrates the cavitation field along a length of shank 200 and FIG. 7B provides a close-up view of the cavitation field of FIG. 7A proximate to a portion of shank 200 that includes the grooves 242 and the grooves 243. In FIGS. 7A-7B, regions of high cavitation probability in the medium surrounding the shank 200 are indicated by the dot-dashed lines and respectively occur in the vicinity of the grooves 242 and the grooves 243.

The cavitation fields are determined using the following equation:

$$G_A \approx \frac{p}{\rho c \Delta \upsilon}$$

in which $G_A$ is the dimensionless cavitation number (typically less than 2), p is the calculated pressure in the tissue, $\rho$ is the tissue density, c is the acoustic velocity of the tissue, and $\Delta v$ is the calculated particle velocity of the tissue.

In an embodiment, spatial locations of cavitation volumes created by grooves of a shank (e.g., shank 200) may be changed by varying a frequency of the ultrasonic energy driving the shank. By way of example, as discussed above with respect to FIGS. 4A-4H, a number of displacement antinode positions and locations of such positions may be varied by varying a frequency of the ultrasonic energy driving a shank. The grooves represent discrete deviations in cross-sectional area, which may be positioned along the shank to substantially coincide with displacement antinode positions that correspond to regions at which maximum interactions between propagating ultrasonic energy and proximate medium occur, as discussed above with respect to FIGS. 5A-5B. As such, by varying a frequency of the ultrasonic energy driving a shank, spatial locations of cavitation volumes created by distinct sets of grooves may be changed.

For example, an ultrasonic source may be coupled to the embodiment of the shank illustrated by FIG. 8 in which multiple grooves may extend along an entire length of the shank 200 of shaft 230. At an initial time, the ultrasonic source coupled to the shank illustrated by FIG. 8 may be caused to generate ultrasonic energy corresponding to an odd integer multiple of the quarter wavelength (e.g., the 0.75 wavelength resonance of FIG. 4B) of the resonance frequency. At the initial time, a groove 844 positioned at approximately a "0.35" normalized length position of the shank, coinciding with a displacement antinode position, may create a cavitation volume in the medium proximate to the "0.35" normalized length position responsive to the ultrasonic energy at the initial time.

At a subsequent time, the ultrasonic source may be caused to generate ultrasonic energy corresponding to a different odd integer multiple of the quarter wavelength (e.g., the 1.25 wavelength resonance of FIG. 4C) of the resonance frequency. To the extent that the "0.35" normalized length position no longer coincides with a displacement antinode position responsive to the second ultrasonic energy, the groove 844 may cease to create cavitation volumes in the proximate medium. However, a groove 845 positioned at approximately a "0.20" normalized length position, coinciding with a displacement antinode position, may create a cavitation volume in the medium proximate to the "0.20" normalized length position responsive to the ultrasonic energy at the subsequent time. Also, a groove 846 positioned at approximately a "0.60" normalized length position coinciding with another displacement antinode position may create cavitation volumes in the medium proximate to the "0.60" normalized length position responsive to the ultrasonic energy at the subsequent time.

With reference to FIGS. 9 and 10, the tip 222 of shank 200 may include a port 347 configured to provide egress for the lumen 345 disposed within shank 200. The port 347 may be located, for example, on a rounded side surface of the tip 222 (FIG. 9) or may be located at the end of the tip 222 (FIG. 10). In an embodiment, the lumen 345 is configured to be coupled to an external source of suction. In an embodiment, the external source of suction may be operated to cause it to apply suction to the medium (e.g., biological tissue of a patient during a cosmetic procedure) via the port 347.

The terminology used herein is for the purpose of describing particular embodiments only and is not intended to be limiting of the embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising."

References herein to terms modified by language of approximation, such as "about", "approximately", and "substantially", are not to be limited to the precise value specified. The language of approximation may correspond to the precision of an instrument used to measure the value and, unless otherwise dependent on the precision of the instrument, may indicate +/−10% of the stated value(s).

While all of the invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed:

1. A probe comprising:
a shank including a proximal end, a distal end, and a shaft extending from the proximal end to the distal end, the proximal end of the shank configured to be coupled to a source of ultrasonic energy, and the shank being configured to propagate the ultrasonic energy from the proximal end to a tip at the distal end in a propagation direction parallel to a longitudinal axis of the shank;
a first groove within the shaft, the first groove positioned proximate to the tip; and
a second groove within the shaft, the second groove positioned along the shank between the first groove and the proximal end,
wherein the shaft includes a non-grooved section between the first groove and the second groove, the first groove is spaced from the second groove by a first distance approximately equal to a first integer multiple of a half-wavelength of a resonance frequency of the shank in the propagation direction, and the first groove is located proximate to a first location at which the ultrasonic energy corresponds to a first odd integer multiple of a quarter wavelength of the resonance frequency.

2. The probe of claim 1 wherein the tip is positioned relative to the proximal end to substantially coincide with a first displacement antinode position when the ultrasonic energy corresponds to an odd integer multiple of a quarter wavelength of the resonance frequency of the shank.

3. The probe of claim 2 wherein the proximal end is configured to be coupled to the source of ultrasonic energy at a point that substantially coincides with a second displacement node position when the ultrasonic energy corresponds to the odd integer multiple of the quarter wavelength of the resonance frequency of the shank.

4. The probe of claim 1 wherein the second groove is located proximate to a second location at which the ultrasonic energy corresponds to a second odd integer multiple of a quarter wavelength of the resonance frequency.

5. The probe of claim 1 wherein the first groove is included in a first plurality of grooves, and the second groove is included in a second plurality of grooves.

6. The probe of claim 4 wherein the shank in the non-grooved section has an outer surface with a first diameter, and the shaft at a first position of each of the first plurality of grooves has a second diameter that is less than the first diameter.

7. The probe of claim 6 wherein the shaft at a second position of each of the second plurality of grooves has a third diameter that is less than the first diameter, and the second diameter is equal to the third diameter.

8. The probe of claim 5 wherein the shaft has an outer surface with a first diameter, the shaft includes a plurality of flanges that project from the outer surface, each of the first plurality of grooves is positioned between an adjacent pair of the plurality of flanges, and the shaft at a position of each of the first plurality of grooves has a second diameter that is equal to the first diameter.

9. The probe of claim 1 wherein the shaft further includes a third groove intervening between the second groove and the proximal end, and the first groove is spaced from the third groove by a second distance approximately equal to a second integer multiple of a half-wavelength of the resonance frequency of the shank in the propagation direction.

10. The probe of claim 1 wherein the shank includes a lumen extending from the distal end to the proximal end, and the tip includes a port coupled to the lumen.

11. The probe of claim 10 wherein the lumen is configured to be coupled to an external source of suction.

* * * * *